United States Patent [19]

Peterson

[11] Patent Number: 5,391,551
[45] Date of Patent: Feb. 21, 1995

[54] METHOD OF LOWERING BLOOD LIPID LEVELS

[75] Inventor: Michael J. Peterson, Waterford, Conn.

[73] Assignee: Pfizer Inc., New York, N.Y.

[21] Appl. No.: 59,688

[22] Filed: May 10, 1993

[51] Int. Cl.⁶ .................... A61K 31/495; A61K 31/50
[52] U.S. Cl. ..................... 514/248; 514/824
[58] Field of Search ................ 514/248, 824

[56] References Cited

U.S. PATENT DOCUMENTS

| | | | |
|---|---|---|---|
| 4,492,706 | 1/1985 | Kallai-Sanfacon | 424/270 |
| 4,868,301 | 9/1989 | Mylari et al. | 544/237 |
| 4,939,140 | 7/1990 | Larson et al. | 514/222 |
| 5,064,830 | 11/1991 | Going | 514/252 |

FOREIGN PATENT DOCUMENTS 0310931  4/1989  European Pat. Off. .

OTHER PUBLICATIONS

P. B. Inskeep et al., Pharm. Res., vol. 8, No. 12, 1511–15, 1991.

B. Tesfamariam et al., J. Cardiovasc. Pharmacol., vol. 21, No. 2, 205–11, 1993.

*Primary Examiner*—Marianne M. Cintins
*Assistant Examiner*—Minna Moezie
*Attorney, Agent, or Firm*—Peter C. Richardson; Gregg C. Benson; James T. Jones

[57] ABSTRACT

A method of lowering blood lipid levels, comprising administering to a patient in need of such treatment an effective amount of a compound of formula I

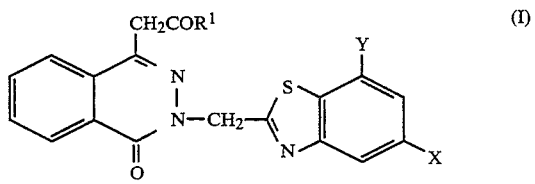

or a pharmaceutically acceptable salt thereof, wherein
$R^1$ is hydroxy or a group capable of being removed in vivo to produce a compound of formula I wherein $R^1$ is OH; and X and Y are the same or different and are selected from hydrogen, trifluoromethyl, fluoro, and chloro.

6 Claims, No Drawings

METHOD OF LOWERING BLOOD LIPID LEVELS

FIELD OF THE INVENTION

This invention relates to the use of certain benzothiazolylmethyl-substituted phthalazineacetic acids, and to certain derivatives thereof, to lower lipid levels in human patients.

BACKGROUND OF THE INVENTION

The compound zopolrestat, 3,4-dihydro-4-oxo-3-(5-trifluoromethylbenzothiazol-2-ylmethyl)phthalazin-1-ylacetic acid, is known, for example from commonly assigned U.S. Pat. No. 4,939,140 to Larson et al., together with a number of compounds related thereto, to have utility as aldose reductase inhibitors. Zopolrestat has the structure

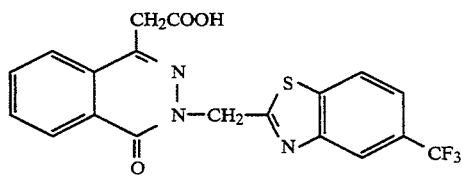

and, as an aldose reductase inhibitor, is useful in the treatment of certain chronic complications arising from diabetes mellitus.

U.S. Pat. No. 4,492,706 to Kallai-Sanfacon teaches that certain aldose reductase inhibitors such as N-[(6-methoxy-5-trifluoromethyl-1-naphthalenyl)thiono]-N-methylglycine (commonly known as tolrestat) function as antilipogenic agents in mammals.

EP 0 310 931 A2 discloses the use of a group of compounds, as antilipogenic agents in poultry, including tolrestat, having the formula

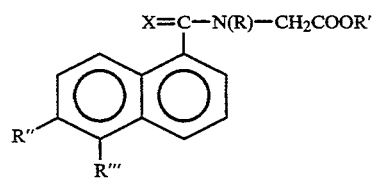

wherein R is an alkyl group of 1–6 carbons, R' is hydrogen or a saturated hydrocarbyl group, R" is hydrogen, hydroxy, or an alkoxy group of 1–6 carbons, R''' is hydrogen or $((CF_2)_nCF_3$, X is sulfur or oxygen, and n is zero or an integer of at least one. This EP application further discloses a poultry feed containing an antilipogenic agent having the above formula.

SUMMARY OF THE INVENTION

This invention provides a method of lowering lipid levels comprising administering to a patient, in need of such treatment, an effective amount of a compound of formula I

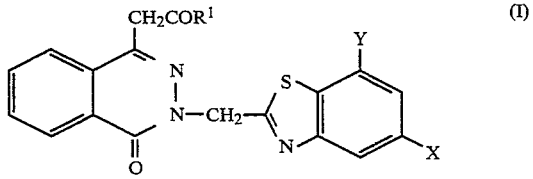

or a pharmaceutically acceptable salt thereof, wherein
$R^1$ is hydroxy or a group capable of being removed in vivo to produce a compound of formula I wherein $R^1$ is OH; and
X and Y are the same or different and are selected from hydrogen, trifluoromethyl, fluoro, and chloro.

The term "lipid-lowering" as employed herein refers to the lowering of blood triglycerides. Compounds of formula 1 are useful as lipid-lowering agents in man and, in particular, they effect a marked reduction in the blood values of triglycerides. On the basis of these lipid-lowering properties the compounds can be used in human medicine for the treatment and prophylaxis of diseases caused by an increased level of triglycerides in the blood. Such diseases are primarily cardiovascular disorders including, inter alia, thrombosis, arteriosclerosis, myocardial infarction and angina pectoris.

Compounds useful in this invention are well suited to the treatment of diabetics because the compounds are aldose reductase inhibitors. Thus this invention is particularly advantageous for treatment to lower lipid levels in patients who are diabetic. The invention is also well suited for use with non-diabetic patients who can benefit from lipid-lowering treatment for non-diabetic conditions such as those enumerated above. Particular compounds which are useful in the method provided by this invention include (with reference to pertinent values in formula I in brackets):

A) 3,4-dihydro-4-oxo-3-(5-trifluoromethylbenzothiazol-2-ylmethyl)phthalazin-1-ylacetic acid [$R^1$=hydroxy; X=$CF_3$; Y=H];

B) 3,4-dihydro-3-(5-fluorobenzothiazol-2-ylmethyl)-4-oxophthalazin-1-yl-acetic acid [$R^1$=hydroxy; X=F; Y=H];

C) 3-(5,7-difluorobenzothiazol-2-ylmethyl)-3,4-dihydro-4-oxophthalazin-1-ylacetic acid [$R^1$=hydroxy; X=Y=F];

D) 3-(5-chlorobenzothiazol-2-ylmethyl)-3,4-dihydro-4-oxophthalazin-1-ylacetic acid [$R^1$=hydroxy; X=Cl; Y=H]; and E) 3-(5,7-dichlorobenzothiazol-2-ylmethyl)-3,4-dihydro-4-oxophthalazin-1ylacetic acid [$R^1$=hydroxy; X=Y=Cl].

Zopolrestat, compound (A) above, is particularly preferred.

DETAILED DESCRIPTION OF THE INVENTION

A group that is capable of being removed in vivo to produce a compound of formula I wherein $R^1$ is hydroxy includes ester forming groups, such as benzyloxy, di($C_1$-$C_4$)alkylaminoethyloxy, acetoxymethoxy, pivaloyloxymethoxy, phthalidoyl, ethoxycarbonyloxyethoxy, 5-methyl-2-oxo-1,3-dioxol-4-ylmethoxy, ($C_1$-$C_4$)alkoxy optionally substituted by morpholino and amide-forming groups such as di($C_1$-$C_4$)alkylamino.

Compounds of formula I can be made as described in the aforementioned U.S. Pat. No. 4,939,140 and in U.S. Pat. No. 4,868,301, both of which are incorporated herein by reference. Thus, as a summary description of the methodology presented therein, the compounds useful in this invention can be made by:

A. reacting a compound of the formula

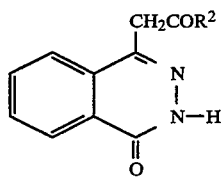

wherein $R^2$ is hydroxy or lower alkoxy such as methoxy or ethoxy, with a compound of the formula

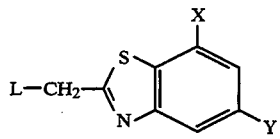

wherein L is a leaving group, and optionally thereafter if $R^2$ is alkoxy, hydrolyzing the alkoxy group to form hydroxy, for example in an aqueous solution of an alkali metal hydroxide. The leaving group L can be, for example, chloro, bromo, or $OSO_2R^6$, wherein $R^6$ is $(C_1-C_4)$alkyl, trifluoromethyl, phenyl, or phenyl substituted by methyl, chloro, bromo, or nitro;

B. reacting a compound of the formula

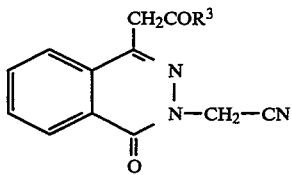

wherein $R^3$ is hydroxy or $(C_1-C_4)$alkoxy, with an acid addition salt of a suitably X- and Y-substituted 2-aminothiophenol.

Particulars of the above reactions, including solvent, temperature, catalysts, and procedures for making and/or sources of precursors can be obtained from the aforementioned U.S. Pat. Nos. 4,939,140 and 4,868,301.

Compounds of formula (I) wherein $R^1$ is hydroxyl may be esterified by conventional methods such as reaction of the corresponding acid chloride, bromide, or anhydride with $R^1H$ to obtain corresponding compounds of formula I wherein $R^1$ is an ester group such as alkoxy. Alternatively, the compounds of formula (I) in which $R^1$ is an ester group may be prepared by alkylating a solution of the sodium salt of a compound (I) wherein $R^1$ is hydroxy. The alkylating agent may be a chloride. For instance when a value for $R^1$ of benzyloxy, acetoxymethoxy, or pivaloyloxymethoxy is desired, then the alkylating agent is benzyl chloride, chloromethylacetate or chloromethylpivalate, respectively. The sodium salt can be generated in situ by reacting a compound of formula (I) wherein $R^1$ is hydroxy with a sodium salt-forming compound such as sodium bicarbonate, sodium hydride, or sodium t-butylammonium sulfate in a non-aqueous solvent such as dimethylformamide or methylpyrrolidone.

When $R^1$ in the compounds of formula (I) is an amide group such as di($C_1-C_4$)alkylamino, a compound of formula (I) wherein $R^1$ is ($C_1-C_4$)alkoxy is converted to the corresponding amide by reaction with a corresponding amine, e.g., a di($C_1-C_4$)alkylamine.

It will be appreciated by those skilled in the art that when $R^1$ is hydroxyl, it is possible to form base addition salts, and pharmaceutically acceptable base salts are intended to be within the scope of the invention. It is also possible to form acid addition salts and these are also intended to be within the scope of the invention.

The pharmaceutically acceptable base addition salts of compounds of formula (I) wherein $R_1$ is hydroxy may be formed with pharmaceutically acceptable cations by conventional methods. Thus, these salts can be readily prepared by treating the compound of formula (I) with an aqueous solution of the hydroxide of the desired pharmaceutically acceptable cation and evaporating the resulting solution to dryness, preferably under reduced pressure. Alternatively, a lower alkyl alcohol solution of the compound of formula (I) may be mixed with an alkoxide of a desired metal cation and the solution subsequently evaporated to dryness. Suitable pharmaceutically acceptable cations for this purpose include, but are not limited to, alkali metal cations such as potassium and sodium, ammonium or water-soluble amine addition salts such as N-methylglucamine (meglumine), the lower alkanolammonium and other base salts with organic amines which are pharmaceutically acceptable, and alkaline earth metal cations such as calcium and magnesium. In general, the sodium and N-methylglucamine salts are preferred.

The pharmaceutically acceptable acid addition salts of the compounds of formula (I) can be prepared in a conventional manner by treating a solution or suspension of the free base (I) with about one chemical equivalent of a pharmaceutically acceptable acid. Conventional concentration and recrystallization techniques are employed in isolating the salts. Illustrative of suitable acids are acetic, lactic, succinic, maleic, tartaric, citric, gluconic, ascorbic, benzoic, cinnamic, fumaric, sulfuric, phosphoric, hydrochloric, hydrobromic, hydroiodic, sulfamic, sulfonic such as methanesulfonic, benzensulfonic, and related acids. Preferably, the acid is phosphoric acid.

A compound of formula (I) can be administered to a subject in need of treatment by a variety of conventional routes of administration, including orally and parenterally, with oral administration being preferred. In general, a compound of formula (I) will be administered to a patient so that an effective daily dose is received, generally a once-daily dose between about 125 mg and 1250 mg, preferably a dose of about 1000 mg per day. However, some variation in dosage will necessarily occur depending on the condition of the subject being treated. The person responsible for administration will, in any event determine the appropriate dose for the individual subject.

A compound of formula (I) may be administered alone or in combination with pharmaceutically acceptable carriers, in either single (e.g., once-daily) or multiple doses. Suitable pharmaceutical carriers include inert solid diluents or fillers, sterile aqueous solution and various organic solvents. A pharmaceutical composition formed by combining a compound of formula (I) and a pharmaceutically acceptable carrier can be readily administered in a variety of dosage forms such as tablets, powders, lozenges, syrups, injectable solutions and the like. These pharmaceutical compositions can, if desired, contain additional ingredients such as flavorings, binders, excipients and the like. For purposes of the preferred route of oral administration, tablets containing various excipients such as sodium citrate, calcium carbonate and calcium phosphate may be employed along with various disintegrants such as starch, alginic acid and certain complex silicates, together with binding agents such as polyvinylpyrrolidone, sucrose, gelatin and acacia. Additionally, lubricating agents such as magnesium stearate, sodium lauryl sulfate and talc are often useful for tabletting purposes. Solid compositions of a similar type may also be employed as fillers in soft and hard filled gelatin capsules. Preferred materials for this include lactose or milk sugar and high molecular weight polyethylene glycols. When aqueous suspensions or elixirs are desired for oral administration, the essential active ingredient therein may be combined with various sweetening or flavoring agents, coloring matter or dyes and, if desired, emulsifying or suspending agents, together with diluents such as water, ethanol, propylene glycol, glycerin and combinations thereof.

For parenteral administration, solutions of the novel compound of formula (I) in sesame or peanut oil, aqueous propylene glycol, or in sterile aqueous solution may be employed. Such aqueous solutions should be suitably buffered if necessary and the liquid diluent first rendered isotonic with sufficient saline or glucose. These particular aqueous solutions are especially suitable for intravenous, intramuscular, subcutaneous and intraperitoneal administration. In this connection, the sterile aqueous media employed are all readily available by standard techniques known to those skilled in the art.

The invention will now be illustrated by the following example which is not, however, to be taken as limiting.

A clinical study was conducted in which the effect of zopolrestat as a lipid lowering agent was assessed. Patients for the study were composed of men and women of non-child bearing potential suffering from diabetic peripheral symmetrical polyneuropathy. The study design included a two-week, single-blind placebo baseline period which preceded a 12 week double-blind treatment period during which patients received either a placebo or zopolrestat, 1000 mg (omni die), by random allocation. There were 146 patients in the group randomized to zopolrestat and 143 patients in the group randomized to placebo.

Blood triglycerides from the study were analyzed by conventional methodology on an Olympus analyzer. By the reagent system employed, triglycerides in a sample are hydrolyzed by lipase to free fatty acids and glycerol. The glycerol is phosphorylated by adenosine-5'-triphosphate (ATP) in the presence of glycerokinase. The resulting glycerol-3-phosphate is oxidized by glycerolphosphate oxidase to dihydroxyacetone phosphate and hydrogen peroxide oxidizes the chromogen, consisting of 4-aminoantipyrine and 3-hydroxy-2,4,6-tribromobenzoic acid to form a red chromogen which is read at a primary wavelength of 540 nm. The color formation is proportional to the concentration of triglycerides and free glycerol present. This absorbance value is then compared to the absorbance produced by a known calibrator with the result being printed out directly.

For the study noted above, mean baseline triglyceride levels for the zopolrestat and placebo groups (in mg/dl) were 304.56 and 269.51, respectively. The mean changes during the double-blind treatment period were $-50.39$ mg/dl and $-1.45$ mg/dl for the zopolrestat and placebo groups, respectively. These differences were statistically significant ($P=0.0052$) based on analyses of covariance to adjust for baseline differences in triglyceride levels.

What is claimed is:

1. A method of lowering blood lipid levels in humans, comprising administering to a human in need of such treatment an effective amount of a compound of formula I

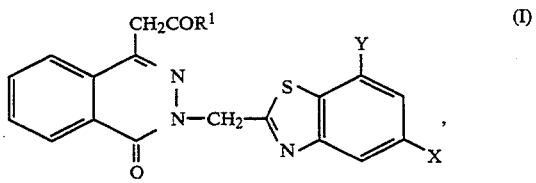

or a pharmaceutically acceptable salt thereof, wherein
$R^1$ is hydroxy or a group capable of being removed in vivo to produce a compound of formula I wherein $R^1$ is OH; and
X and Y are the same or different and are selected from hydrogen, trifluoromethyl, fluoro, and chloro.

2. A method as defined in claim 1, wherein said compound is selected from
A) 3,4-dihydro-4-oxo-3-(5-trifluoromethylbenzothiazol-2-ylmethyl)phthalazin-1-ylacetic acid;
B) 3,4-dihydro-3-(5-fluorobenzothiazol-2-ylmethyl)-4-oxophthalazin-1-ylacetic acid;
C) 3-(5,7-difluorobenzothiazol-2-ylmethyl)-3,4-dihydro-4-oxophthalazin-1-ylacetic acid;
D) 3-(5-chlorobenzothiazol-2-ylmethyl)-3,4-dihydro-4-oxophthalazin-1 -ylacetic acid; and
E) 3-(5,7-dichlorobenzothiazol-2-ylmethyl)-3,4-dihydro-4-oxophthalazin-1-ylacetic acid.

3. A method as defined in claim 2, wherein said compound is zopolrestat, compound A.

4. A method as defined in claim 1 wherein the compound is administered orally.

5. A method as defined in claim 2 wherein the compound is administered orally.

6. A method as defined in claim 3 wherein the compound is administered orally.

* * * * *